United States Patent [19]
Duan et al.

[11] Patent Number: 5,736,504
[45] Date of Patent: Apr. 7, 1998

[54] PERFUME COMPOSITION

[75] Inventors: Xiao Guang Duan, Falkirk, Great Britain; Eric Jacques P. C. Dumas, Utrecht; Johannes Helmond, Gouda, both of Netherlands

[73] Assignee: Unichema Chemie B.V., Gouda, Netherlands

[21] Appl. No.: 702,481

[22] PCT Filed: Feb. 15, 1995

[86] PCT No.: PCT/EP95/00556

§ 371 Date: Dec. 24, 1996

§ 102(e) Date: Dec. 24, 1996

[87] PCT Pub. No.: WO95/23842

PCT Pub. Date: Sep. 8, 1995

[30] Foreign Application Priority Data

Mar. 2, 1994 [EP] European Pat. Off. ............ 94200524

[51] Int. Cl.$^6$ ..................................... A61K 7/46
[52] U.S. Cl. .................. 512/1; 512/4; 252/108; 252/174.11
[58] Field of Search ............... 572/1, 2, 4; 252/174.11, 252/108

[56] References Cited

U.S. PATENT DOCUMENTS

| | | | |
|---|---|---|---|
| 4,584,126 | 4/1986 | Joshi | 252/368 |
| 4,879,063 | 11/1989 | Wood-Rethwell et al. | 252/370 |
| 5,082,600 | 1/1992 | Smith et al. | 252/547 |
| 5,310,495 | 5/1994 | Hill et al. | 252/118 |
| 5,496,489 | 3/1996 | Dussault et al. | 252/134 |
| 5,529,714 | 6/1996 | Tokosh | 252/108 |

FOREIGN PATENT DOCUMENTS 40 02 873  4/1991  Germany ................................ 512/1

OTHER PUBLICATIONS

Patent Abstract of Japan, vol. 16, No. 13, (C-0901) Jan. 14, 1992, & JP,A,03 234797, Oct. 18, 1991 (see abstract).

*Primary Examiner*—James H. Reamer
*Attorney, Agent, or Firm*—Pillsbury Madison & Sutro LLP

[57] ABSTRACT

A perfume or fragrance composition to be incorporated into translucent or transparent soap comprises a saturated or unsaturated, straight or branched chain carboxylic acid having from 6 to 22 carbon atoms and at least one carboxyl group, preferably iso-stearic acid, as a translucency enhancer. The invention also relates to a process of preparing perfumed, translucent or transparent soap, and the soap thus obtained.

3 Claims, No Drawings

PERFUME COMPOSITION

BACKGROUND OF THE INVENTION

This application claims benefit of international application PCT/EP95/00556, filed Feb. 15, 1995.

The present invention relates to a perfume or fragrance composition to be incorporated into translucent or transparent soaps, as well as to a process for preparing a perfumed, translucent or transparent soap, and to translucent or transparent soap noodles or tablets thus obtained.

Transparent and translucent soaps have an aesthetic appeal to the consumer and have been associated with purity and hence with "naturalness". The essential difference between transparent and translucent soap is related to the relative quality of the light transmitted. By "transparent" is understood having the property of transmitting light without appreciable scattering, so that objects placed behind a transparent soap bar are entirely visible and can easily be discerned.

By "translucent" is understood having the property of allowing light to pass through partially or diffusely so that objects placed behind a translucent soap bar cannot clearly be distinguished (therefore also called partly transparent or semi-transparent).

In the present specification and the attached claims the translucency is evaluated by measuring the light transmission of a slice of soap having a thickness of 18.5 mm before and after the preparation according to the present invention, using a reflectometer according to Dr B. Lange, Type LMG 008. The result is expressed as a percentage of the light transmission of a matted glass standard. The transmission of the glass standard compared to air is 8.3% and this transmission of the standard is taken as 100%.

Although for coloured soap there is some dependence on the colour, this difference can be neglected for non-coloured soap bars or tablets.

There are two basic manufacturing methods for making translucent and/or transparent soaps, the one route is called the "solvent method" and the other the "mechnical working" method.

In the "solvent method", a dried conventional type of toilet soap in solid form is dissolved in boiling ethanol, or the saponification is effected in an ethanol-water mixture. If a clear solution is obtained, the major part of the ethanol is removed by evaporation to form a clear, viscous soap solution. This is poured into moulds and cooled. The solidified soap is pressed out into the desired shape and is placed for many weeks in conditioning rooms. During conditioning more water and alcohol is evaporated and consequently the final product becomes firm. The disadvantages of this process are the long duration of the process and all the disadvantages of working with volatile and toxic solvents, which also from an ecological point of view is disadvantageous.

Another method used is the so-called "semi-boiled" process, in which a suitable blend of fatty materials is reacted with a strong solution of sodium hydroxide in a closed mixing vessel. Only water vapour is allowed to escape and upon completion of the saponification process, the liberated glycerol is retained in the final soap. After addition of the required other ingredients, the final warm and viscous soap solution is poured into moulds for rapid cooling, which enhances transparency. Hereafter the products are shaped (stamped) and packaged.

The "mechanical working" methods involve some sort of intensive mechanical working or shearing of a cooled and partially dried soap base. It is usual to add effective amounts of crystallization inhibitors to the liquid soap before drying in order to enhance translucency. Translucency is only achieved after mechanical working or shearing to a considerable degree, e.g. by mixing in a Z-blade mixer, or by multiple milling using 3, 4 or 5-rolled steel mills, or by using a cavity transfer mixer. Such processes have been described in U.S. Pat. No. 2,970,116 (Lever Brothers Company) and European Patent Specification EP-B-0,090,649 (Unilever). Another method is the use of "super" refiners, where the partially translucent soap is forced through a series of fine perforated plates or sieves by which translucency is imparted. One of the disadvantages of this method is that shear-sensitive additives under the prevailing conditions of temperature and pressure can be seriously reduced in quality, so that their performance in the final product is far from optimal. Moreover the bars obtained are translucent and usually not transparent and there are limitations in the production in that the soap needs extensive recycling over the production line in order to get the right temperature and the required amount of shear. Also the soap tends to stick to the stamping dies.

One of the problems in preparing translucent or transparent soaps is the incorporation of perfumes or fragrances into the soap, because this needs careful handling. The perfume or fragrance will normally include a transparent essential oil, such as geraniol or sandalwood oil, and an intensifying agent and often will also comprise a synthetic perfume, such as artificial musk, and a solvent, such as benzyl alcohol, and the like. Usually the perfume composition is incorporated into the soap, typically at a level of 0.8 to 1.5% by weight, based on the total soap composition. The perfume needs to be of an alkali-resistant type, however, and it should be non-irritant to the skin and economical in use.

Generally, perfume has a negative effect on the translucency, however, and it has been found that a number of perfumes cause the translucency of the soap to markedly decrease. Such perfumes are defined as "bad perfumes" for translucent or transparent soap. The introduction of a new perfume or fragrance with slightly different solubility characteristics in the soap may frequently introduce a serious reduction in transparency. There is therefore a need for a perfume or fragrance composition which irrespective the perfume composition can be used in translucent or transparent soaps without impairing the translucency of the final perfumed soap.

SUMMARY OF THE INVENTION

It has now been found during extensive experiments that the incorporation of effective amounts of certain carboxylic acids into the perfume or fragrance composition may lead to markedly enhanced translucency if such a perfume or fragrance composition is incorporated into the soap. Even if "bad perfumes" were used, the incorporation of the translucency enhancer resulted in increased translucency.

Therefore, the present invention relates to a perfume of fragrance composition to be incorporated into translucent or transparent soap, which is characterized in that the composition comprises an effective amount of a translucency enhancer.

DETAILED DESCRIPTION

Preferably, the translucency enhancer is a saturated or unsaturated, straight or branched chain carboxylic acid having from 6 to 22 carbon atoms and having at least one carboxyl group. Also mixtures of such acids may be used.

Preferably the translucency enhancer is iso-stearic acid or hydrogenated, structurally modified monomeric fatty acid obtained in the polymerization of at least mono-unsaturated fatty acids having from 8 to 22 carbon atoms (for a method of preparing such acid see U.S. Pat. No. 2,812,342 (Peters)).

In general, the amount of translucency enhancer is from 25% to 95% by weight, preferably from 30% to 80% by weight, of the total perfume or fragrance composition. It is possible to use smaller amounts e.g. 15% by weight under specific conditions.

It is known from Japanese Patent Application JP-A-05/202,396 (Lion Corp.) to incorporate perfume into a soap base by separately forming a molten mixture of the perfume and a $C_6$–$C_{18}$ fatty acid and cooling this mixture, and subsequently blending this perfume concentrate with the soap. The purpose of forming the blend of perfume and fatty acid is to keep the perfume in the soap upon storage and to release the perfume form the soap in a controlled way. It has nowhere been described or even suggested in this publication, however, that the use of $C_6$–$C_{18}$ fatty acid in combination with the perfume leads to enhanced translucency of the soap, even if the perfume as such would be a "bad perfume", i.e. would normally reduce the translucency of the soap. In fact, there is no reference at all to translucent or transparent soap in this publication.

The soap comprises a mixture of soluble soaps and insoluble soaps. By "soluble" soaps are to be understood throughout this specification and the attached claims: the salts of saturated monocarboxylic acids or fatty acids having from 8 to 14 carbon atoms and additionally the salts of oleic acid and polyunsaturated monocarboxylic or fatty acids having from 8 to 22 carbon atoms. By "insoluble" soaps are to be understood throughout this specification and the attached claims: the salts of saturated monocarboxylic or fatty acids having from 16 to 24 carbon atoms. The salts of the monocarboxylic or fatty acids are preferably sodium salts, but small amounts of potassium soaps, ammonium soaps or alkanolamine soaps may also be present. The selection of the soaps depends on availability and cost, but suitable soaps are derived from coconut oil, palm kernel oil, tallow, hydrogenated tallow, palm oil, and the like and mixtures thereof. It is preferred to use soaps prepared from 70–80% tallow and 20–30% coconut oil, palm oil and/or palm kernel oil.

The translucent or transparent soap into which the perfume or fragrance composition according to the present invention may be incorporated may also comprise a polyhydric alcohol, such as propylene glycol, glycerol, polyethylene glycols and mixtures of polyhydric alcohols. The use of glycerol and/or sorbitol is preferred. Also sugars or at least partially hydrogenated sugars may be used. Preferably form 5% to 15% by weight of the total soap composition of polyhydric alcohol and/or sugar is used.

The soap material may also comprise an effective amount of one or more synthetic or non-soap detergents, which may be of the anionic, nonionic, amphoteric or cationic type, or mixtures thereof. Usually, up to 25% by weight of the total composition of synthetic or non-soap detergent is used.

Suitable cationic detergents include quaternary ammonium compounds, such as stearyl dimethyl benzyl ammonium chloride, and the like.

Suitable amphoteric detergents include the alkyl-β-iminodipropionates and iminopropionates and long-chain imidazole derivatives, such as imidazolinium betaines.

Suitable anionic detergents include the alkyl aryl sulphonates, such as $C_{10}$–$C_{22}$ alkyl benzene sulphonates; the olefin sulphonate salts; the $C_{10}$–$C_{20}$ paraffin sulphonate salts; The $C_8$–$C_{22}$ fatty acyl sarconsinates; the $C_8$–$C_{22}$ fatty acyl isethionates and $C_8$–$C_{22}$ fatty acyl N-methyl taurides; the $C_8$–$C_{22}$ fatty acid alkanol amides; the $C_8$–$C_{20}$ alkyl sulphates and the sulphate esters of the reaction product of 1–20 moles of an alkylene oxide with 2 to 5 carbon atoms and a saturated straight-or branched-chain aliphatic monohydric $C_8$–$C_{20}$ alcohol, such as sodium lauryl ether sulphate.

Suitable nonionic detergents include the reaction products of 1–50 moles of $C_2$–$C_4$ alkylene oxide with $C_8$–$C_{20}$ primary or secondary alkanols, with dihydric alcohols, and the like.

The soap may also comprise up to 25% by weight of the total composition of a crystallization modifier, such as hydroxystearic acid, dimerized and/or trimerized fatty acid, elaidic acid and their alkali metal soaps.

Finally, the soap may also comprise up to 20% by weight of the total composition of hydrotropes, such as triethanolamine, amine soaps and surfactants.

Also effective amounts of functional additives may be present. The functional additive may be selected from the group consisting of antioxidants, such as tocopherols, BHA, BHT and the like; chelating agents, such as EDTA and the like; colouring agents; deodorants; dyes; emollients, such as cosmetic oils; enzymes; foam boosters, which may be selected from anionic, amphoteric, nonionic and certain cationic surfactants, such as sodium cocoyl isethionate, sodium lauryl ether sulphate, lauric acid diethanolamide, and the like; foam stabilizers; germicides; lathering agents; moisturizers; optical brighteners; dyes; pearlescers; sequestering agents; skin conditioners, such as dimerized fatty acids; solvents such as propylene glycol, glycerol, sorbitol, and the like; stabilizers; superfatting agents, such as fatty acids; UV absorbers and mixtures of these functional additives.

The functional additives may be used in any desired quantity to effect the desired functional characteristics, and usually minor amounts from about 0.01% by weight up to 10% by weight are used. Some of the additives may be used in larger amounts, however.

The perfume or fragrance compositions according to the present invention should preferably be of an alkali-resistant type, which implies that esters are less preferred components of the perfume composition. Also the perfume should be free from allergic reactions generating components and be non-irritant to the skin. A certain degree of substantivity to the skin may be desirable. Furthermore the composition should, be stable upon storage of the soap into which it has been incorporated and it should not cause coloration or discoloration in the soap under the influence of light and/or elevated temperatures.

Perfume components are for example alcohols, like geraniol, citronellol, linalool, and the like; ketones, like ionone; phenyl ethers, like safrole, synthetic perfume components, like musk, but also other types,.such as essential oils, like oils of geranium, bergamot, violet, lemon, patchouli oil, and the like. The use of citrus-like perfuming material is preferred.

Usually the perfume or fragrance compositions are blends made from a large number of different compounds in order to arrive at a stable, balanced perfume, which is not all at once being released from the soap upon use or during storage, but is released in a rather controlled manner upon use of the soap.

The perfume or fragrance composition according to the present invention is used in the transparent or translucent soap in an amount of from 0.3% to 10% by weight, preferably from 0.5% to 5% by weight, of the total soap composition.

The present invention therefore also relates to a process of preparing a perfumed, transparent or translucent soap, which is characterized in that from 0.3% to 10% by weight (based upon the total soap composition) of a perfume or fragrance composition according to the present invention is incorporated into the soap.

The present invention also relates to translucent or transparent soap tablets or noodles comprising a perfuming amount of the perfume or fragrance composition according to the present invention.

Finally, the present invention also relates to the use of saturated or unsaturated, straight or branched chain carboxylic acids, having from 6 to 22 carbon atoms and at least one carboxyl group as a translucency enhancer in perfume or fragrance compositions to be used in transparent or translucent soaps.

The invention will now further be illustrated on hand of the following examples.

EXAMPLE I (a) Preparation of translucent soap without additives

A soap formulation was prepared, consisting of: 56.4% by weight of sodium soap of tallow fatty acids, 14.1% by weight of sodium soap of palm kernel fatty acids, 2.5% by weight of free palm oil fatty acids, 5% by weight of sorbitol, 7% by weight of glycerol and 13.9% by weight of water.

After mixing 5 kg of this soap composition with 55 g of water (to have the water level at 15% by weight), the temperature of the soap composition was 22° C. Then the soap composition was passed through a laboratory Mazzoni M-100 duplex refiner/plodder with refining sieves of 0.5 mm and provided with a rectangular extrusion die of 45 mm ×19 mm at the end of the conical outlet. The cylinder temperatures were set at 30° C. and the cone temperature was 57° C. The speed of the plodder screw was fixed at 2.5 (related to rotation speed). The temperature of the composition after six passages through the duplex refiner/plodder was 43.5° C. The output velocity was 35.1 kg/h. The translucency of a soap tablet obtained from this composition was 18.3%. The temperatures and translucencies after each passage through the refiner plodder were as follows:

| Cycle | Temperature of soap (°C.) | Translucency of tablet (in %) |
| --- | --- | --- |
| 1 | 30.8 | 0.9 |
| 2 | 36.0 | 1.3 |
| 3 | 37.8 | 2.4 |
| 4 | 40.3 | 4.9 |
| 5 | 41.4 | 13.0 |
| 6 | 43.5 | 18.3 |

The translucency was evaluated by measuring the light absorption of a Slice of soap having a thickness of 18.5 mm and expressing this value as a percentage of the light transmission of a matted glass standard, using a reflectometer. The transmission of the standard compared to air is 8.3% and this value is taken as 100% throughout the measurements. A translucency value of 15 is generally rated as acceptable for translucent soap.

(b) Soap with translucency enhancer only

The same soap formulation as described above sub (a) was used, 55 g of water was mixed with the soap composition for 5 min. and 50 g (1% by weight) of isostearic acid was mixed with the soap composition for another 5 min. The temperature after the mix was 22° C. The soap composition was recycled by following the same procedure as described above sub (a) under the same conditions. After six recycles, the translucency of a soap tablet obtained from this composition was 27.7%, the temperature of the soap bar was 43.3° C. and the output velocity was 51.6 kg/h.

The temperatures and translucencies measured after each passage or cycle were as follows:

| Cycle | Temperature of soap (°C.) | Translucency of tablet (in %) |
| --- | --- | --- |
| 1 | 35.0 | 1.1 |
| 2 | 37.1 | 1.6 |
| 3 | 39.2 | 4.6 |
| 4 | 41.2 | 10.1 |
| 5 | 42.1 | 19.8 |
| 6 | 43.3 | 27.7 |

(c) Soap with perfume only

The same soap formulation as described above sub (a) was used, 55 g of water was mixed with the soap composition for 5 min. and 50 g (1% by weight) of perfume Uniff 1 (ex International Flavors & Fragrances, The Netherlands) was mixed with the soap composition for another 5 min. The temperature after mixing was 22° C. The soap composition was recycled by following the same procedure as described sub (a) under the same conditions. After six recycles, the translucency of a soap tablet obtained from this composition was 24.3%, temperature of the soap bar was 43.2° C. and the output velocity was 43.2 kg/h. The temperatures and translucencies measured after each passage or cycle were as follows:

| Cycle | Temperature of soap (°C.) | Translucency of tablet (in %) |
| --- | --- | --- |
| 1 | 34.0 | 1.1 |
| 2 | 37.1 | 2.2 |
| 3 | 39.0 | 3.9 |
| 4 | 40.4 | 6.8 |
| 5 | 41.6 | 17.3 |
| 6 | 43.2 | 24.3 |

(d) Soap with perfume and translucency enhancer

The same soap formulation as described sub (a) was used, 55 g of water was mixed with the soap composition for 5 min. and 100 g (2% by weight) of perfume Blend A, which was prepared by mixing Uniff 1 (as described sub (c)) and isostearic acid in a weight ratio of 1:1, was mixed with the soap composition for another 5 min. The temperature after mixing was 22° C. The soap composition was recycled by following the same procedure as described in sub (a) under the same conditions. After six recycles, the translucency of a soap tablet obtained from this composition ws 43.9%. the temperature of the soap bar was 44.2° C. and the output velocity was 48.3 kg/h.

The temperatures and translucencies measured after each passage or cycle were as follows:

| Cycle | Temperature of soap (°C.) | Translucency of tablet (in %) |
| --- | --- | --- |
| 1 | 35.5 | 1.3 |
| 2 | 37.3 | 2.8 |
| 3 | 39.5 | 10.3 |

| Cycle | Temperature of soap (°C.) | Translucency of tablet (in %) |
| --- | --- | --- |
| 4 | 42.0 | 26.4 |
| 5 | 43.0 | 35.1 |
| 6 | 44.2 | 43.9 |

From the experiments 1(a), 1(b), 1(c) and 1(d) it can clearly be seen that the addition of the translucency enhancer to the perfume leads to a synergism in the translucency value of the soap tablet.

EXAMPLE II (a) Soap with perfume

The same soap formulation as in Example I (a) was used, 55 g of water was mixed with the soap composition for 5 min. and 50 g (1% by weight) of perfume Coconut 48733 (ex Fragrance Oils (International) Limited Manchester, UK) was mixed with the soap composition for another 5 min. The temperature after mixing was 22° C. The soap composition was recycled by following the same procedure as described in Example I (a) under the same conditions. After six recycles, the translucency of a soap tablet obtained from this composition was 10.7%, temperature of the soap bar was 43.4° C. and the output velocity was 43.2 kg/h.

The temperatures and translucencies measured after each passage or cycle were as follows:

| Cycle | Temperature of soap (°C.) | Translucency of tablet (in %) |
| --- | --- | --- |
| 1 | 31.8 | 1.3 |
| 2 | 34.5 | 1.4 |
| 3 | 38.3 | 2.1 |
| 4 | 40.2 | 3.6 |
| 5 | 41.6 | 7.0 |
| 6 | 43.4 | 10.7 |

(b) Soap with perfume and translucency enhancer

The same soap formulation as in Example I(a) was used, 55 g of water was mixed with the soap composition for 5 min and 100 g (2% by weight) of perfume Blend B, which was prepared by mixing perfume Coconut 48733 with isostearic acid in a weight ratio of 1:1, was mixed with the soap composition for another 5 min. The temperature after mixing was 22° C. The soap composition was recycled by following the same procedure as described in Example I(a) under the same conditions. After six recycles, the translucency of a soap tablet obtained from this composition was 74.2%, temperature of the soap bar was 43.6° C. and the output velocity was 45.6 kg/h.

The temperatures and translucencies measured after each passage or cycle were as follows:

| Cycle | Temperature of soap (°C.) | Translucency of tablet (in %) |
| --- | --- | --- |
| 1 | 33.8 | 1.4 |
| 2 | 35.3 | 2.3 |
| 3 | 38.8 | 5.5 |
| 4 | 41.6 | 22.6 |
| 5 | 42.8 | 36.0 |
| 6 | 43.6 | 74.2 |

Again, the marked synergism in translucency produced in the soap tablet using the perfume/translucency enhancer mixture according to the present invention can be noted.

EXAMPLE III (a) Soap with perfume

The same soap formulation as in Example I(a) was used, 55 g of water was mixed with the soap composition for 5 min and 75 g (1.5% by weight) of perfume C93.8155 (ex Créations Aromatiques Genève, Switzerland) was mixed with the soap composition for another 5 min. The temperature after mixing was 22° C. The soap composition was recycled by following the same procedure as described in Example I(a) under the same conditions. After six recycles, the translucency of a soap tablet obtained from this composition was 19.7%, temperature of the soap bar was 44.2° C. and the output velocity was 54.0 kg/h.

The temperatures and translucencies measured after each passage or cycle were as follows:

| Cycle | Temperature of soap (°C.) | Translucency of tablet (in %) |
| --- | --- | --- |
| 1 | 33.5 | 1.6 |
| 2 | 38.4 | 1.8 |
| 3 | 40.7 | 3.1 |
| 4 | 42.1 | 5.9 |
| 5 | 43.2 | 12.9 |
| 6 | 44.2 | 19.7 |

(b) Soap with perfume and translucency enhancer

The same soap formulation as in Example I(a) was used, 55 g of water was mixed with the soap composition for 5 min and 125 g (2.5% by weight) of perfume Blend C, which was prepared by mixing perfume C93.8155 with isostearic acid in a weight ratio of 1.5:1, was mixed with the soap composition for another 5 min. The temperature after mixing was 22° C. The soap composition was recycled by following the same procedure as described in Example I(a) under the same conditions. After six recycles, the translucency of a soap tablet obtained from this composition was 54.8%, temperature of the soap bar was 44.7° C. and the output velocity was 46.8 kg/h.

The temperatures and translucencies measured after each passage or cycle were as follows:

| Cycle | Temperature of soap (°C.) | Translucency of tablet (in %) |
| --- | --- | --- |
| 1 | 37.2 | 1.7 |
| 2 | 38.6 | 4.8 |
| 3 | 40.2 | 6.5 |
| 4 | 42.6 | 22.9 |
| 5 | 43.3 | 31.2 |
| 6 | 44.7 | 54.8 |

The marked synergism obtained in the soap tablet by using the perfume/translucency enhancer according to the present invention can clearly be noticed.

We claim:

1. A perfume or fragrance composition to be incorporated into translucent or transparent soap, characterized in that the composition comprises an effective amount of iso-stearic acid.

2. A process of preparing a perfumed, translucent or transparent soap, comprising incorporating from 0.3% to 10% by weight (based upon the total soap composition) of a perfume or fragrance composition according to claim 1 into the soap.

3. A process according to claim 2, characterized in that from 0.5% to 5% by weight (based on the total soap composition) of said perfume or fragrance composition is incorporated into the soap.

* * * * *